United States Patent
Lee et al.

(10) Patent No.: US 10,368,808 B2
(45) Date of Patent: Aug. 6, 2019

(54) SYSTEM AND METHODS OF DETERMINING ETIOLOGY OF UNDIAGNOSED SYMPTOMATIC EVENTS

(71) Applicant: Medtronic Monitoring, Inc., San Jose, CA (US)

(72) Inventors: Brian B. Lee, Golden Valley, MN (US); ShaileshKumar V. Musley, Blaine, MN (US); Robert W. Stadler, Shoreview, MN (US); Maneesh Shrivastav, Blaine, MN (US); Randal Schulhauser, Phoenix, AZ (US); Stacie Vilendrer, Santa Rosa, CA (US)

(73) Assignee: Medtronic Monitoring, Inc., San Jose, CA (US)

(*) Notice: Subject to any disclaimer, the term of this patent is extended or adjusted under 35 U.S.C. 154(b) by 317 days.

(21) Appl. No.: 15/341,465

(22) Filed: Nov. 2, 2016

(65) Prior Publication Data
US 2018/0116598 A1 May 3, 2018

(51) Int. Cl.
*A61B 5/00* (2006.01)
*A61B 5/022* (2006.01)
(Continued)

(52) U.S. Cl.
CPC .......... *A61B 5/7264* (2013.01); *A61B 5/0022* (2013.01); *A61B 5/022* (2013.01);
(Continued)

(58) Field of Classification Search
CPC ....... A61B 5/045; A61B 5/046; A61B 5/0472; A61B 5/022; A61B 5/023; A61B 5/7264
See application file for complete search history.

(56) References Cited

U.S. PATENT DOCUMENTS 6,416,471 B1 7/2002 Kumar et al.
6,719,701 B2* 4/2004 Lade .................... A61N 1/3622
600/481
(Continued)

OTHER PUBLICATIONS

"Withings Wireless Blood Pressure Monitor" http://store.apple.com/us/product/HF047ZM/A/withings-wireless-blood-pressuremonitor?afid=p238|XPDdhifzdc_mtid_1870765e38482_pcrid_52243355290_&cid=aos-US-kwg-pla-btb, last viewed on Oct. 10, 2016.
(Continued)

*Primary Examiner* — Meredith Weare
(74) *Attorney, Agent, or Firm* — Billion & Armitage; Michael A. Collins

(57) ABSTRACT

Embodiments describe a method of determining etiology of undiagnosed events comprising monitoring electrocardiogram signals and blood pressure of a patient via a medical device, capturing one or more of an ECG segment and a BP reading in response to a triggering event, classifying one or more of the ECG segment and BP reading as normal or abnormal, and determining etiology of undiagnosed symptomatic events based on the classification. Embodiments further describe a medical device comprising sensors for monitoring ECG signals and BP of a patient, circuitry for capturing one or more of ECG segments and BP readings of a patient in response to a triggering event, and a processor for communicating one of more of captured ECG segments and captured BP readings to a remote monitoring center directly or indirectly where the captured ECG segments and captured BP readings are classified as normal or abnormal.

20 Claims, 7 Drawing Sheets

(51) Int. Cl.
| | |
|---|---|
| A61B 5/145 | (2006.01) |
| A61B 5/11 | (2006.01) |
| A61B 5/103 | (2006.01) |
| A61B 5/0408 | (2006.01) |

(52) U.S. Cl.
CPC ........ *A61B 5/04085* (2013.01); *A61B 5/1032* (2013.01); *A61B 5/1116* (2013.01); *A61B 5/14532* (2013.01); *A61B 5/7282* (2013.01); *A61B 5/04087* (2013.01); *A61B 5/6832* (2013.01); *A61B 2560/0412* (2013.01)

(56) References Cited

U.S. PATENT DOCUMENTS

| | | | |
|---|---|---|---|
| 6,873,870 | B2 | 3/2005 | Ferek-Petric |
| 7,233,822 | B2 | 6/2007 | Hettrick et al. |
| 8,180,440 | B2 | 5/2012 | McCombie et al. |
| 8,538,510 | B2 | 9/2013 | Toledo et al. |
| 8,626,275 | B1 | 1/2014 | Amit et al. |
| 8,688,190 | B2 | 4/2014 | Libbus et al. |
| 8,706,201 | B2 | 4/2014 | Beker et al. |
| 8,862,211 | B2 | 10/2014 | Toledo et al. |
| 9,060,683 | B2 | 6/2015 | Tran |
| 9,167,980 | B2 | 10/2015 | Ben-David et al. |
| 9,254,096 | B2 | 2/2016 | Schultz |
| 2003/0167012 | A1* | 9/2003 | Friedman ............... A61B 5/021 600/506 |
| 2006/0030782 | A1 | 2/2006 | Shennib |
| 2006/0247686 | A1 | 11/2006 | Girouard |
| 2009/0076345 | A1* | 3/2009 | Manicka ............... A61B 5/0205 600/301 |
| 2010/0228103 | A1* | 9/2010 | Schecter ............... A61B 5/4094 600/301 |
| 2011/0040197 | A1* | 2/2011 | Welch ................... A61B 5/0205 600/509 |
| 2013/0035604 | A1 | 2/2013 | Yu |
| 2016/0113533 | A1 | 4/2016 | Ben-David et al. |
| 2016/0128595 | A1 | 5/2016 | Fischell |
| 2016/0287174 | A1 | 10/2016 | Joseph |
| 2017/0265782 | A1* | 9/2017 | Vollmer ............... A61B 5/0205 |

OTHER PUBLICATIONS

Readmissions Reducation Program. Centers for Medicare and Medicaid Services. <http://www.cms.gov/Medicare/Medicare-Fee-for-Service-Payment/AcuteInpatientPPS/Readmissions-Reduction-Program.html>, last viewed on Nov. 2, 2016.

Abboud, et al., "A spectral analysis of the high frequency QRS potentials observed during acute myocardial ischemia in dogs.", Int J Cardio.l 1990; 26, 285.

Abboud, et al., "Detection of transient myocardial ischemia by computer analysis of standard and signal-averaged high-frequency electrocardiograms in patients undergoing percutaneous transluminal coronary angioplasty.", Circulation. 1987; 76, 585.

Abboud, et al., "High frequency electrocardiography of three orthogonal leads in dogs during a coronary artery occlusion.", PACE. 1989; 12, 574.

Abboud, et al., "High frequency electrocardiography using an advanced method of signal averaging for non-invasive detection of coronary artery disease in patients with conventional electrocardiogram.", J. Electrocardiol 1985; 19:371-380, 371-380.

Abboud, "High-frequency electrocardiogram analysis of the entire QRS in the diagnosis and assessment of coronary artery disease.", Prog Cardiovasc Dis. 1993; 35, 311.

Aversano, et al., "High frequency QRS electrocardiography in the detection of reperfusion following thrombolytic therapy.", Clin Cardiol. 1994; 17, 175.

Batdorf, et al., "Month-to-Month and Year-to-Year Reproducibility and High Frequency QRS ECG Signals.", Journal of Electrocardiology, vol. 37 No. 4 Oct. 2004, 289-296.

Beker, et al., "Analysis of high frequency QRS potential during exercise testing in patients with coronary artery disease and in healthy subjects.", Pacing Clin Electrophysiol. 1996; 19 (Part 1), 2040-50.

Berklap, et al., "Effects of Percutaneous Transluminal Coronary Angioplasty on Late Potentials and High Frequency Mid-QRS Potentials", Cariology 1994; 85, 216-221.

Bhargava, et al., "Myocardial infarction diminishes both low and high frequency QRS potentials: power spectrum analysis of lead II.", J Electrocardiol. 1981; 14, 57.

Conover, "Understanding Electrocardiography: Arrhythmias and the 12-lead ECG.", The C.V. Mosby Company. Fifth Edition, 1988, 323.

Franz, et al., "Localization of regional myocardial ischemia by recording of monophasic action potentials.", Circulation. 1984; 69(3), 593-604.

Goldberger, et al., "Effect of myocardial infarction on high frequency ECG.", Circulation. 1981; 64, 34.

Goldberger, et al., "Effect of myocardial infarction on the peak amplitude of high frequency QRS potentials.", Journal Electrocardiol 1980; 13, 367-372.

Hanninen, et al., "Recording locations in multichannel magnetocardiograpy and body surface potential mapping sensitive for regional exercise-induced myocardial ischemia.", Basic Res Cardiol. 2001; 96(4), 405-14.

Howie, "An evaluation of a new two electrode myocardial electrical impedance monitor for detecting myocardial ischemia.", Anesth Analg. 2001; 92(1), 12-8.

Langner, et al., "High-frequency components in the electrocardiograms of normal subjects and of patients with coronary heart disease", AM Heart J. 1961;62, 746-55.

Mason, "A new system of multiple-lead exercise electrocardiography", AM Heart J. 1966; 71, 196.

Matsushita, et al., "High-frequency QRS potentials as a marker of myocardial dysfunction after cardiac surgery.", Ann Thorac Surg 2004; 77, 1293-7.

Mehta, et al., "Sudden death in coronary artery disease: acute ischemia versus myocardial substrate", Circulation. 1997; 96, 3215-3223.

Mor-Avi, et al., "Effects of coronary occlusion on high frequency content of the epicardial electrogram and body surface electrocardiogram", Circulation . 1987; 76(1), 237-243.

Mor-Avi, "Spectral analysis of canine epicardial electrogram. Short-term variations in the frequency contect induced by myocardial ischemia.", Circ Res. 1990; 66, 1681-1691.

Pahlm, et al., "Data processing of exercise ECGs", IEEE Trans Biomed Eng 1987; 34, 158.

Pettersson, et al., "Changes in high-frequency QRS components are more sensitive than ST-segment deviation for detecting acute coronary artery occlusion", J Am Coll Cardiol. 2000; 36, 1827-1834.

Pettersson, et al., "Electrocardiographic changes during prolonged coronary artery occlusion in man: Comparison of standard and high-frequency recordings", Clin Physiol. 1998; 18, 179.

Rahman, et al., "Non-invasive detection of coronary artery disease by a newly developed high-frequency QRS electrocardiogram", Physiol Meas. 2004; 25(4), 957-65.

Ringborn, et al., "The absence of high-frequency QRS changes in the presence of standard electrocardiographic QRS changes of old myocardial infarction", Am Heart J. 2001; 141, 573.

Santopietro, "The origin and characteristics of primary signal noise and interference source in the high frequency electrocardiogram", Proc IEEE. 1976; 65, 707.

Schlegel, et al., "Real-time 12-lead high-frequency QRS electrocardiography for enhanced detection of myocardial ischemia and coronary artery disease", Mayo Clin Proc. 2004;79(3), 339-50.

Sharir, et al., "Use of Electrocardiographic Depolarization Abnormalities for Detection of Stress-Induced Ischemia as Defined by Myocardial Perfusion Imaging", American Journal Cardio 2012; 109, 642-650.

Siegel, et al., "Intracardiac electrode detection of early or subendocardial ischemia", Pacing Clin Electrophysiol. 1982; 6, 892-902.

(56) References Cited

OTHER PUBLICATIONS

Siltanen, et al., Magnetocardiography. Chapter in MacFarlane P, eds: Comprehensive Electrocardiology vol. II. Pergamon Press, 1989, 1405-1438.

Theres, et al., "Comparison of electrocardiogram and intrathoracic electrogram signals for detection of ischemic ST segment changes during normal sinus and ventricular pace rhythms", J Cardiovasc Electrophysiol. 2002; 10, 990-995.

Tragardh, et al., "Reduced high-frequency QRS components in patients with ischemic heart disease compared to normal subjects", J Electrocardiol. 2004; 037(3): 157-62.

Van Der Ark, et al., "Genesis of high frequency notching of QRS complex in an in vivo cardiac model", Circulation. 1975; 51:257.

Zhang, et al., "QRS depolarization based intra-cardiac myocardial ischemia and infarction detection", Heart Rhythm. 2005; Supplement 2(5), Abstract # P2-87.

Zipes, et al., "Sudden cardiac death", Circulation. 1998; 98:2334-2351.

Abboud, "The Use of Cross-Correlation Function for the Alignment of ECG Waveforms and Rejection of Extrasystoles", Computers and Biomedical Research, Oct. 10, 1983, 9 pages.

\* cited by examiner

SYSTEM AND METHODS OF DETERMINING ETIOLOGY OF UNDIAGNOSED SYMPTOMATIC EVENTS

TECHNICAL FIELD

The present disclosure is generally related to medical devices for determining etiology of undiagnosed symptomatic events.

BACKGROUND

Syncope is a medical term for fainting and occurs as a result of a reduction in blood flow and oxygen to the brain. Various types of syncope exist and the severity of each may vary. Neurocardiogenic syncope is a common type of syncope and is often referred to as vasovagal syncope. Neurocardiogenic syncopal episodes generally relate to problems with both the heart and the nervous system. For example, the sight of blood or extreme emotional distress may trigger a neurocardiogenic syncopal episode that causes your heart rate and blood pressure to drop suddenly. Orthostatic hypotension is another type of syncope that may be caused by a sudden drop in blood pressure induced by a change in posture—position, such as when an individual stands upright. Both neurocardiogenic syncope and orthostatic hypotension can are typically harmless and require no treatment. On the other hand, cardiogenic syncope is a more serious type of syncope because, while it can be related to other serious cardiac causes, it generally is related to cardiac arrhythmias (e.g., abnormal heart rhythms) In particular, a syncopal episode that is cardiogenic is generally indicative of a more serious underlying heart problem that requires immediate attention.

Syncopal episodes are intermittent in nature and commonly characterized as a temporary loss of consciousness with a fast onset, short duration, and spontaneous recovery. This makes it difficult to diagnose syncope, which requires a diagnostic workup including various forms of physiological information obtained through, for example, electrocardiogram (ECG) monitoring and blood pressure monitoring, among other things. Due to the intermittent nature of syncope, physiological information at the onset of a syncopal episode useful in a diagnosis is often not available. In addition, collecting this information following a syncopal episode is highly invasive and disruptive to a patient's day-to-day activities. Consequently, syncope of unknown etiology is very common and often misdiagnosed.

It would therefore be desirable to provide a system and method of detecting physiological changes associated with undiagnosed symptomatic events such as syncope in a non-invasive manner.

SUMMARY

In general, embodiments of the present disclosure describe systems and methods of determining etiology of undiagnosed events.

Accordingly, embodiments of the present disclosure describe a method of determining etiology of undiagnosed events. The method includes monitoring electrocardiogram (ECG) signals and blood pressure (BP) of a patient via a medical device. In response to a triggering event, the method further includes capturing one or more of an ECG segment and a BP reading. Upon capturing one or more of an ECG segment and a BP reading in response a triggering event, the method includes classifying one or more of the ECG segment and BP reading as normal or abnormal. The etiology of undiagnosed symptomatic events based on the classification of the ECG segment and/or BP reading is determined.

Embodiments of the present disclosure further describe a medical device comprising sensors for monitoring ECG signals and BP of a patient. The medical device further includes circuitry for capturing one or more of ECG segments and BP readings of a patient in response to a triggering event. The medical device also includes a processor. The process is for communicating one or more of captured ECG segments and captured BP readings to a remote monitoring center directly or indirectly where the captured ECG segments and captured BP readings are classified as normal or abnormal.

The details of one or more examples are set forth in the description below. Other features, objects, and advantages will be apparent from the description and from the claims.

DETAILED DESCRIPTION

The present invention relates to systems and methods of determining etiology of undiagnosed events. In particular, the present invention relates to detecting physiological changes associated with undiagnosed symptomatic and/or asymptomatic events and other conditions by capturing physiological data at the onset of symptomatic and/or asymptomatic events and classifying the captured physiological data as normal or abnormal. Undiagnosed events may include syncope, falls, palpitations, seizures, among other things. Here, a noninvasive medical device is used to capture physiological data, such as electrocardiogram (ECG) segments and blood pressure (BP) readings, in an ambulatory setting, in response to a triggering event. The captured physiological data is analyzed to detect physiological changes with respect to, for example, heart rhythm and blood pressure. Using this analysis, the captured physiological data may be classified as normal or abnormal and relied upon to differentiate between common causes of syncope, such as vasovagal syncope, and more severe causes of syncope, such as cardiogenic syncope. In this way, the present invention improves a diagnosis of syncope and other conditions in patients in a non-invasive manner.

Figure 1:
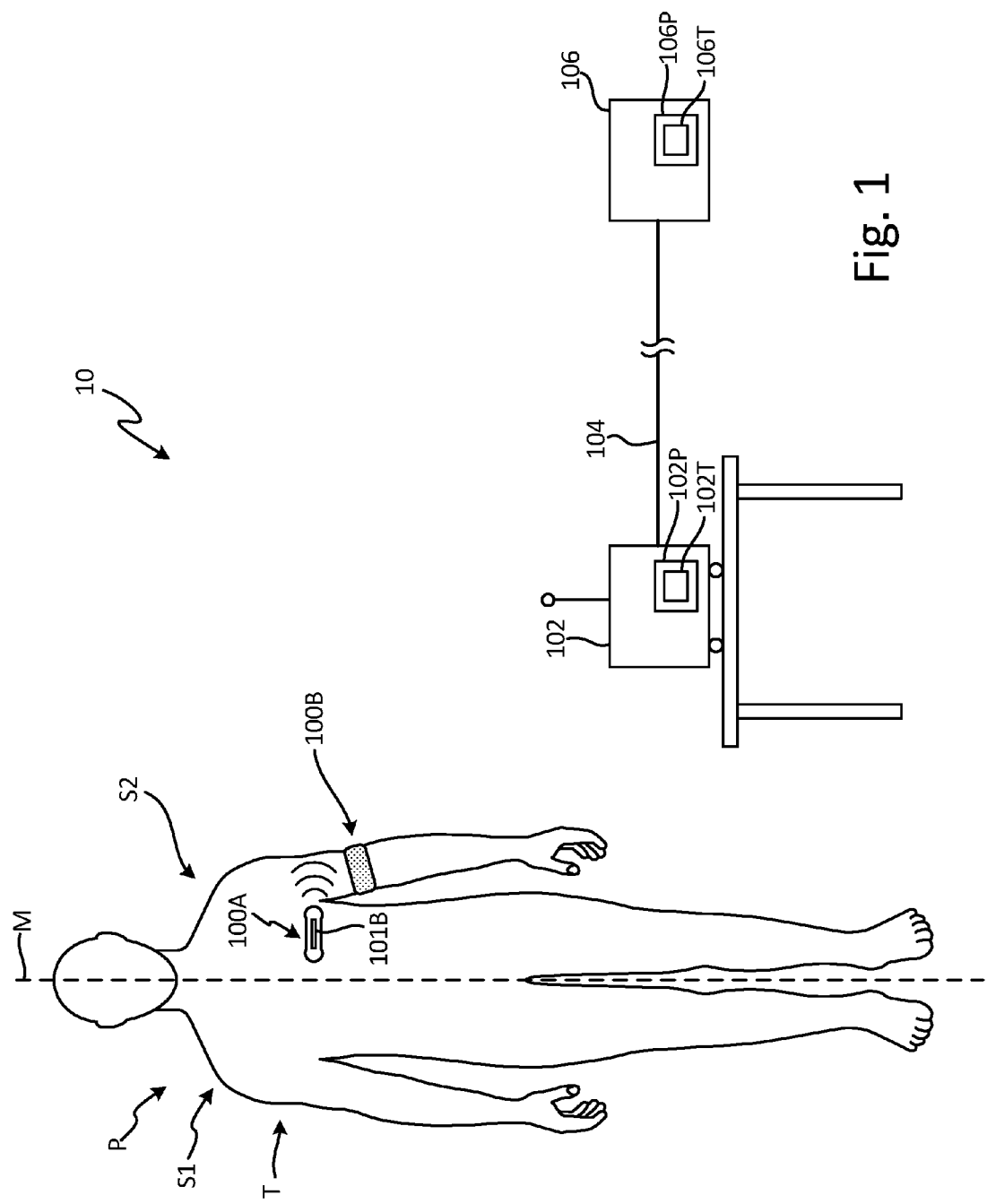
FIG. 1 is a schematic view of a patient and a patient monitoring system, according to one or more embodiments of the present disclosure.

FIG. 1 is a schematic view of a patient P and a monitoring system 10, according to an embodiment of the present disclosure. Patient P includes a midline M, a first side S1 (e.g., a right side), and a second side S2 (e.g., a left side). Monitoring system 10 includes a patient medical device 100, gateway 102, and remote monitoring center 106. In the embodiment shown in FIG. 1, patient medical device 100 includes an adherent device 100A and a sensor 100B. FIG. 1 shows the adherent device 100A attached to the skin of the patient and the sensor 100B being worn by the patient. In other embodiments (not shown in FIG. 1), patient medical device 100 may be an implantable device, an insertable device, an injectable device, a wearable device, such as a Holter monitor (collectively referred to as a medical device), or a combination thereof. Exemplary embodiments of suitable medical devices are described in more detail with respect to FIGS. 1, 5, and 6. In general, medical device 100 is described herein as performing a monitoring function, but in other embodiments may be configured to provide treatment as well.

Medical device 100 can be adhered/injected/inserted/worn by patient P at many locations. In many embodiments, adherent device 100A is adhered to one side of a thorax of patient P, where it monitors ECG signals to detect rhythm abnormalities, and sensor 100B is worn on an arm, a wrist, or a finger of patient P, where blood pressure is monitored to detect blood pressure abnormalities. The location of medical device 100 can vary in other embodiments and depend on the physiological parameters of patient P being monitored. The physiological parameters being monitored by medical device 100 may include electrocardiogram (ECG) signals to detect rhythm abnormalities, such as tachycardia and/or bradycardia, and blood pressure (BP) readings to detect blood pressure abnormalities, as well as activity level data, body posture, bio-impedance, respiration, etc. A benefit of medical device 100 and its various embodiments is that it may be utilized to collect physiological data from the patient at an onset of a syncopal episode while the patient goes about normal day-to-day activities outside of a hospital setting.

Medical device 100 may be a non-invasive medical device that is worn continuously and/or intermittently. In many embodiments, adherent device 100A may be continuously adhered to patient P (e.g., seven (7) to thirty (30) days) and sensor 100B may be intermittently worn by patient P. For example, sensor 100B may be a wearable satellite pressure sensor (e.g., blood pressure cuff) that can be worn on an arm, a wrist, or a finger of the patient. In one embodiment, patient P only wears the blood pressure cuff in response to a patient-triggered event. A patient-triggered event may include instances where patient P triggers capture of physiological data upon experiencing an onset of symptoms. In another embodiment, patient P only wears the blood pressure cuff in response to an automatically triggered event. An automatically triggered event may include instances where adherent device 100A detects asymptomatic events (e.g., abnormal ECG segment) and then prompts (e.g., alerts) patient P to wear the blood pressure cuff to capture BP readings. In other embodiments, patient P continuously wears the blood pressure cuff to capture BP readings in response to automatically triggered events and/or predetermined intervals without patient intervention. In other embodiments, the adherent device and blood pressure cuff are both worn continuously.

While adherent device 100A is also discussed below with respect to FIG. 6, adherent device 100A may include one or more sensors and circuitry for monitoring and/or sensing physiological signals, such as ECG signals. Embodiments of sensor 100B may include a blood pressure cuff. The blood pressure cuff may include pressure sensor elements and a battery, as well as circuitry for wirelessly communicating with other medical device components, including adherent device 100A. In many embodiments, the circuitry communicates with adherent device 100A via Bluetooth connectivity. In other embodiments, circuitry communicates with adherent device 100A via Wi-Fi networks and/or cellular networks. The blood pressure cuff may store and wirelessly transmit monitored and captured blood pressure data to adherent device 100A. At adherent device 100A, blood pressure data is combined with, if available, ECG data and other physiological data and subsequently stored and/or transmitted to, for example, gateway 102 or remote monitoring center 106 for further processing and analysis. In other embodiments, sensor 100B may be a glucose monitor (e.g., a continuous glucose monitor), or an accelerometer.

Processing and analysis of physiological data (e.g., ECG signals/segments and BP data/readings) may be done locally by medical device 100 (e.g., at adherent device 100A), or remotely by gateway 102 and/or remote monitoring center 106 (or similar platform separate from medical device 100). Processing and analysis of physiological data may include monitoring physiological data to detect triggering events, capturing physiological data in response to a triggering event, and classifying the captured physiological data as normal or abnormal. In many embodiments, physiological data may be monitored locally (e.g., at adherent device 100A) for triggering events. Captured physiological data may be transmitted to an external processing center, such as gateway 102 and/or remote monitoring center 106, where it is processed, analyzed, and/or classified as normal or abnormal. Captured physiological data may be transmitted immediately or delayed for a period of time (i.e., until it is possible/cost effective to communicate the data). In some embodiments, once the physiological data is classified, the physiological data may be stored for subsequent review by a physician/expert, the physician/expert may verify the classification and take appropriate steps (e.g., prescribe treatment), and/or the patient P may be alerted of the physiological data classified as abnormal.

In one embodiment, adherent device 100A monitors ECG signals and sensor 100B (e.g., blood pressure cuff) monitors a patient's BP. Monitored BP data may be transmitted from sensor 100B to adherent device 100A, where it is combined with monitored ECG signals and analyzed locally at adherent device 100A for a triggering event (e.g., a patient-triggered event and/or an automatically triggering event). In one embodiment, upon detecting an automatically triggering event, adherent device 100A automatically triggers capture of ECG segments and BP readings. The captured BP readings are transmitted to adherent device 100A, where the captured BP readings are combined with the captured ECG segments. The combined captured data is subsequently communicated to gateway 102 and/or remote monitoring center 106, where it is classified as normal or abnormal and/or stored for subsequent review by a physician/expert. While the above embodiment locally analyzes monitored ECG signals and BP data and remotely analyzes captured ECG segments and BP readings, other embodiments include analyzing monitored ECG signals and BP data remotely, analyzing captured ECG segments and BP readings locally, or any combination thereof.

In another embodiment, adherent device 100A captures ECG segments and sensor 100B (e.g., blood pressure cuff) captures BP readings in response to a patient-triggered event. Captured BP readings may be transmitted from sensor 100B to adherent device 100A, where the captured BP readings are combined with the captured ECG segments. The combined captured data is subsequently communicated to gateway 102 and/or remote monitoring center 106, where it is classified as normal or abnormal and/or stored for subsequent review by a physician/expert. While the above embodiment analyzes captured data remotely, other embodiments include analyzing the captured data locally (e.g., at adherent device 100A).

In the embodiment shown in FIG. 1, sensor 100B communicates wirelessly with adherent device 100A, and adherent device 100A communicates wirelessly with remote center 106. The communication may occur directly (via a cellular or Wi-Fi network, or via Bluetooth connectivity), or indirectly through intermediate device or gateway 102. In one embodiment, ECG signals and/or BP data monitored by medical device 100 are analyzed locally at adherent device 100A and captured ECG segments and/or BP readings are directly or indirectly communicated in their entirety to remote center 106 for analysis. In other embodiments, one or more of ECG signals, BP data, ECG segments, and BP readings may be processed, analyzed, and/or transmitted locally and/or remotely.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example, with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by human experts to verify accuracy. Reports may then be generated at remote monitoring center 106 for communication to the patient's physician or care provider. In one embodiment, in addition to one-way communication from medical device 100 to gateway 102 and/or remote monitoring center 106, remote monitoring center 106 may communicate/push reference data to medical device 100, either to program/initialize medical device 100 or update the reference data stored by medical device 100.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG and BP samples—monitored by medical device 100 and sensor 101 may be analyzed by one or more of the distributed processors included as part of medical device 100, gateway 102, and/or remote monitoring center 106.

Figure 2:
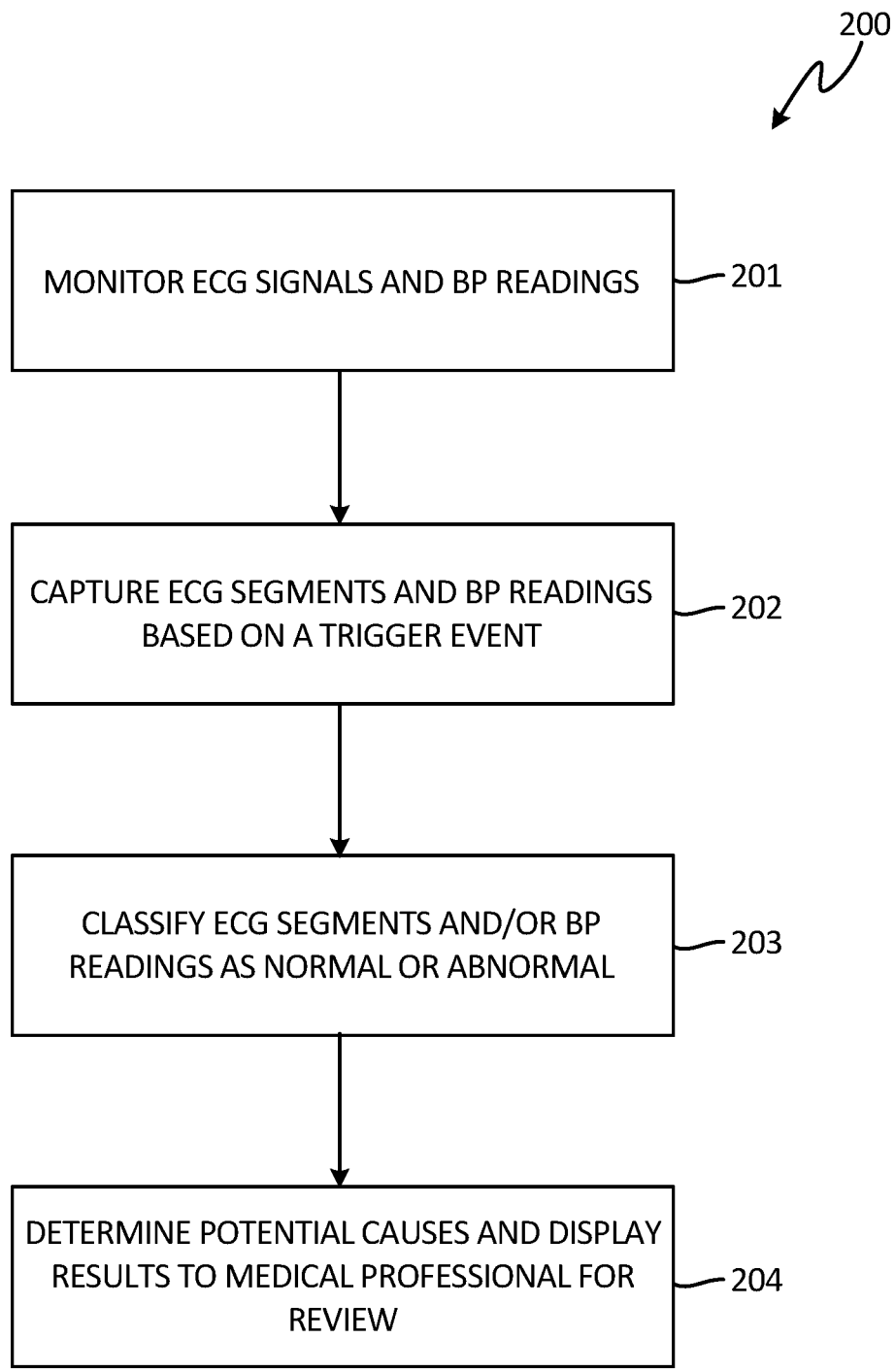
FIG. 2 is a flowchart of a method of determining etiology of undiagnosed events, according to one or more embodiments of the present disclosure.

FIG. 2 is a flowchart of a method of determining etiology of undiagnosed events, according to an embodiment of the present invention. Any of the medical devices of the present disclosure may be utilized to implement the method illustrated in FIG. 2.

At step 201, physiological data are monitored via a medical device. In one embodiment, the medical device includes an adherent device and a blood pressure cuff. According to this embodiment, the adherent device may monitor ECG signals including heart rate of a patient and the blood pressure cuff may monitor the BP of a patient. In other embodiments, the medical device may include additional components for monitoring other types of physiological data, including one or more of glucose levels, pulse pressure, posture/position including falls and sudden changes in posture, and epidermal pigment coloration. For example, a continuous Bluetooth monitor may be utilized for the purpose of detecting significant changes in glycemic profile that may affect a change in BP and/or heart rate.

At step 202, physiological data are captured in response to a triggering event. In some embodiments, the physiological data captured includes prospective physiological data (e.g., data captured following a triggering event). In other embodiments, the physiological data that is captured includes recent physiological data previously stored in memory (e.g., "looping" memory). For example, looping memory may include physiological data captured about 15 minutes before the triggering event. The period of time over which recent physiological data is stored may be greater than and/or less than 15 minutes. In these embodiments, recent physiological data may be utilized where an event has already passed by the time a triggering event is detected and/or confirmed. In some embodiments, the physiological data captured may include prospective physiological data and recent physiological data stored in looping memory.

Generally, triggering events may include patient-triggered events and/or automatically triggered events. Patient-triggered events may include symptomatic events in which a patient experiences an onset of symptoms and manually triggers capture of physiological data. In one embodiment, a patient experiencing an onset of symptoms may manually trigger capture of ECG segments and/or BP readings. In other embodiments, a patient may trigger capture of any type of physiological data upon experiencing an onset of symptoms.

Automatically triggered events may include asymptomatic events in which the medical device, upon monitoring and/or detecting physiological data defining an automatically triggering event, automatically triggers (e.g., without human intervention) the capture of physiological data. In some embodiments, automatically triggered events occur upon detecting a change in physiological data relative to baseline physiological data, or baseline data. Baseline data generally refers to data utilized with respect to triggering events. In some embodiments, baseline data includes threshold levels and/or changes in physiological levels. Threshold levels include, but are not limited to, heart rate thresholds, such as an upper heart rate limit and a lower heart rate limit, and blood pressure thresholds, such as an upper blood pressure limit and a lower blood pressure limit. Changes in physiological levels include, but are not limited to, ECG changes, heart rate changes, heart rhythm changes, and blood pressure changes. Threshold levels and physiological levels (e.g., baseline levels/data) for determining changes in levels may be based on population-based data (e.g., population-based ECG data) and/or patient-specific baseline data (e.g., patient-specific baseline BP data). In some embodiments, population-based data and/or patient-specific data may include data relating to heart rhythm, heart rate, ECG morphology, and blood pressure. In some embodiments, baseline data includes capturing posture and/or position data with a patient in an upright position. In other embodiments, baseline data includes reference physiological data as described below.

At step 203, the captured physiological data is classified as normal or abnormal. In general, captured physiological data is compared to reference physiological data in order to classify captured data as normal or abnormal. In one embodiment, the captured data is generally analyzed to detect rhythm abnormalities (i.e., arrhythmia, etc.) and/or blood pressure abnormalities (i.e., sudden increases and/or decreases in blood pressure). Reference physiological data, or reference data, generally refers to data utilized in classifying captured physiological data as normal or abnormal. In some embodiments, reference data includes previously captured physiological data, which may include physiological data collected daily or less frequently, as well as physiological data collected more recently, such as within the last 15 minutes. In some embodiments, captured ECG segments are compared to previously captured ECG segments and classified as abnormal if an abnormal heart rhythm or a significant ECG change is detected. In some embodiments, captured blood pressure readings are compared to previously captured BP readings and classified as abnormal if a significant BP change is detected. In other embodiments, reference physiological data includes one or more of previously captured ECG data (e.g., ECG segments), previously captured BP data (e.g., BP data), and any of the baseline data including threshold levels and changes in physiological levels described above.

In many embodiments, monitored and captured physiological data is combined and transmitted to remote monitoring center 106 directly or indirectly through gateway 102 for further processing and analysis relating to classifying the physiological data as normal or abnormal. However, in some embodiments, monitored and captured physiological data is combined and transmitted to remote monitoring center 106 directly or indirectly through gateway 102 for review by a human expert/physician.

At step 204, potential causes and results, including captured ECG segments and BP readings are displayed and communicated to a medical professional for review. In addition, a potential cause of undiagnosed conditions in a patient is identified based on the combination of one or more types of physiological data and the classification of physiological data as normal or abnormal. In one embodiment, step 204 may indicate and/or rule out one or more different potential causes of undiagnosed conditions in a patient. An abnormal ECG segment and abnormal BP reading may indicate a rhythm disturbance. An abnormal ECG segment and normal BP reading may indicate an arrhythmia-related disturbance, which may be noted for future analysis. A normal ECG segment and abnormal BP reading may indicate other causes, such as neurocardiogenic syncope, orthostatic hypotension, dehydration, and other neurogenic causes. A normal ECG segment and a normal BP reading may indicate that consideration of other causes is appropriate. In some embodiments, the captured physiological data and classification thereof as normal or abnormal is communicated to a medical professional for review. In some embodiments, step 204 is optional.

Figure 3:
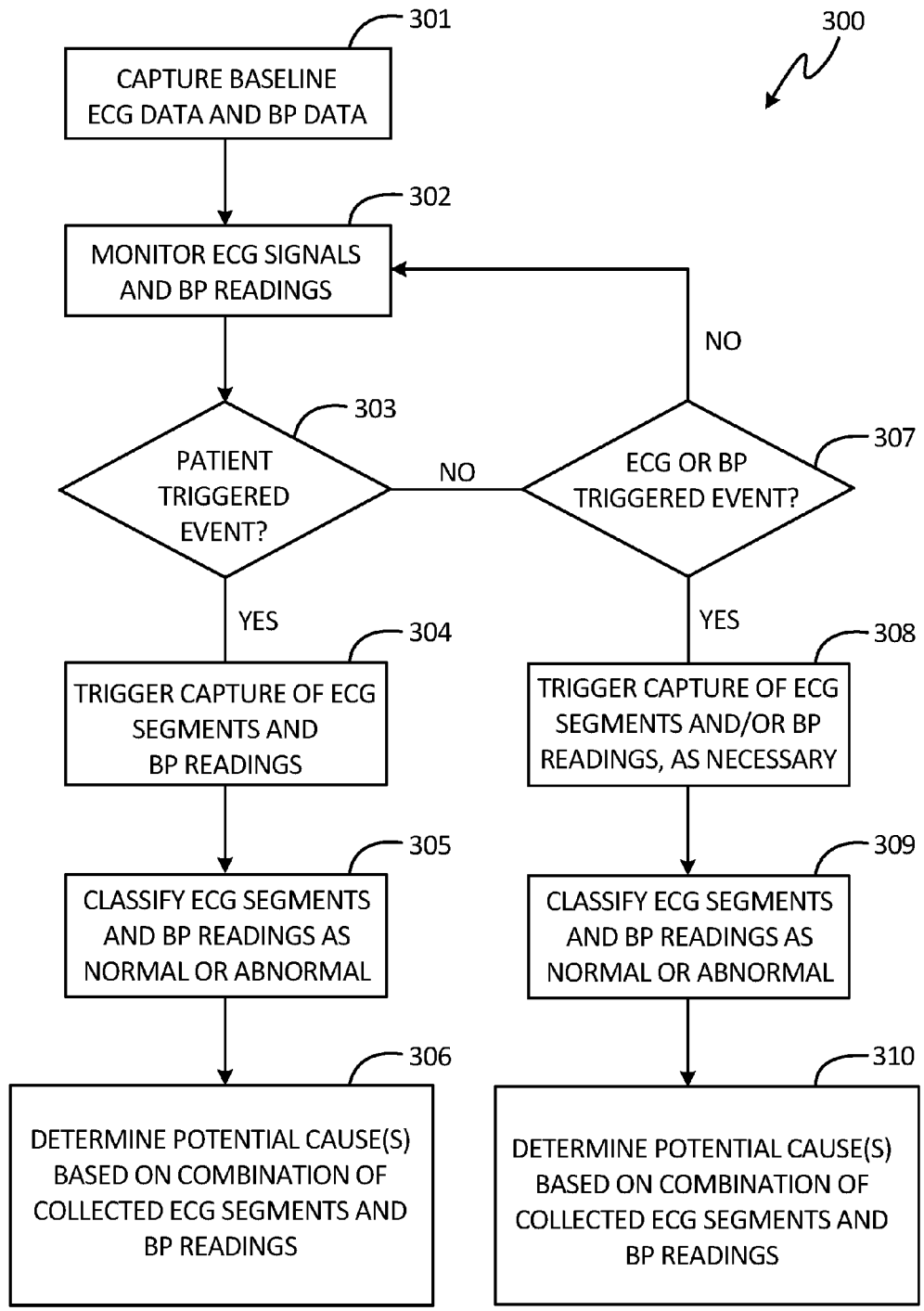
FIG. 3 is a flowchart of a method of determining etiology of undiagnosed events for patient triggered events and electrocardiogram/blood pressure triggered events, according to one or more embodiments of the present disclosure.

FIG. 3 is a flowchart of a method of determining etiology of undiagnosed events, according to an embodiment of the present invention. Any of the medical devices provided in the present disclosure may be utilized to implement the method illustrated in FIG. 3.

At step 301, baseline data is captured (e.g., collected and stored). In many embodiments, baseline data may be used to automatically trigger the capture of physiological data (e.g., ECG segments and BP readings). Baseline data may be collected as needed, but typically baseline data is collected at the time a patient is fitted with a medical device with the assistance of a medical professional (e.g., physician). In addition, baseline data may be renewed periodically (e.g., daily) and may be obtained when the patient is known to be in a resting state. In some embodiments, a resting state may include one or more of low activity level, horizontal posture, and low heart rate. In other embodiments, baseline data may be obtained when the patient is not in a resting state. In some embodiments, baseline data is stored locally (e.g., on adherent device) where it is processed and/or analyzed for automatically triggering events. In other embodiments, baseline data may be stored remotely at remote monitoring center 106 where it may be reviewed by a physician/expert.

At step 302, physiological signals are monitored as described above with respect to FIGS. 1 and 2. In one embodiment, ECG signals including heart rate and blood pressure are monitored. At decision steps 303 and 307, the medical device detects automatically triggered events and patient-triggered events, respectively. In some embodiments, decision step 303 may confirm a patient-triggered event occurred and the method 300 may proceed to step 304. In some embodiments, decision step 303 may detect and/or confirm no patient-triggered event occurred and the method 300 may proceed to decision step 307 to detect and/or confirm an automatically triggered event. In some embodiments, decision step 307 may detect and/or confirm an automatically triggered event occurred and the method 300 may proceed to step 308. In some embodiments, decision step 307 may detect and/or confirm that no automatically triggered event occurred and the method 300 may proceed and/or return to step 302. In other words, in some embodiments, neither a patient-triggered event, nor an automatically triggered event is detected and/or confirmed, in which case the method 300 returns to step 302 and repeats the above loop.

Generally, with respect to step 303, if a patient-triggered event is detected and/or confirmed, the method 300 proceeds to step 304 and the medical device captures physiological data. In some embodiments, the medical device utilizes recent physiological data stored in memory (e.g., "looping" memory) of recent recordings. In this embodiment, recent physiological data may be utilized where an event has already passed by the time the patient-triggered event is detected and/or confirmed. In some embodiments, the medical device captures ECG segments and/or BP readings in response to a patient-triggered event. In many embodiments, both ECG segments and BP readings are captured in response to a patient-triggered event. For instance, in the absence of an automatically triggered event, it is useful to capture both ECG segments and BP readings to increase the type and amount of information available to aid in diagnosis. While this embodiment generally relates to ECG segments and BP readings, any type of physiological data provided in the present disclosure may be captured at this step.

Generally, with respect to step 307, if monitored physiological data is above or below a threshold level, or if monitored physiological data indicates a significant change in a physiological level, the method 300 proceeds to step 308 and the medical device automatically triggers capture of the relevant physiological data (e.g., non-triggering physiological data). In some embodiments, at step 308, the relevant physiological data that is captured includes recent physiological data stored in memory (e.g., looping memory) of recent recordings. Physiological data that is relevant depends on the triggering event. In some embodiments, automatically triggering events may be designated as an ECG triggered event and/or a BP triggered event. For example, if monitored ECG signals are above a heart rate threshold in a case of tachycardia or below a heart rate threshold in a case of bradycardia, an ECG triggered event is observed and in this instance the relevant physiological data captured is BP. In such a case, capturing ECG segments may be unnecessary because, as a practical matter, the occurrence of the ECG triggered event, alone, may be a sufficiently reliable indicator of an abnormal ECG. In other words, the ECG is presumed abnormal in instances where the automatically triggering event is an ECG triggered event. In another example, for BP triggered events, such as a sudden increase and/or decrease in blood pressure, the relevant physiological data captured is ECG segments. In this instance, capturing BP readings may be unnecessary because the occurrence of a BP triggered event, alone, may be a sufficiently reliable indicator of an abnormal BP. While the above embodiments may only capture non-triggering physiological data at step 308, other embodiments capture both triggering and non-triggering physiological data at step 308.

At steps 305 and 309, captured physiological data is classified as normal or abnormal based on reference physiological data, as described above with respect to FIG. 2. In particular, as described above with respect to FIG. 2, reference data, which may be different from baseline data, generally includes previously captured physiological data. For example, in some embodiments, the captured physiological data includes captured ECG segments and/or captured BP readings, and the captured ECG segments and/or captured BP readings are classified as normal or abnormal based on previously captured ECG segments and/or previously captured BP readings. In other embodiments, the captured physiological data is classified as normal or abnormal based on baseline data, the details of which are provided above with respect to FIG. 2.

Steps 306 and 310 are optional. As provided above with respect to FIG. 2, the combination of captured ECG segments and captured BP readings and classifications corresponding to the captured ECG segments and captured BP readings, respectively, may be utilized and/or relied upon to determine a potential cause of undiagnosed conditions in a patient, such as syncope and/or other conditions.

Figure 4A:
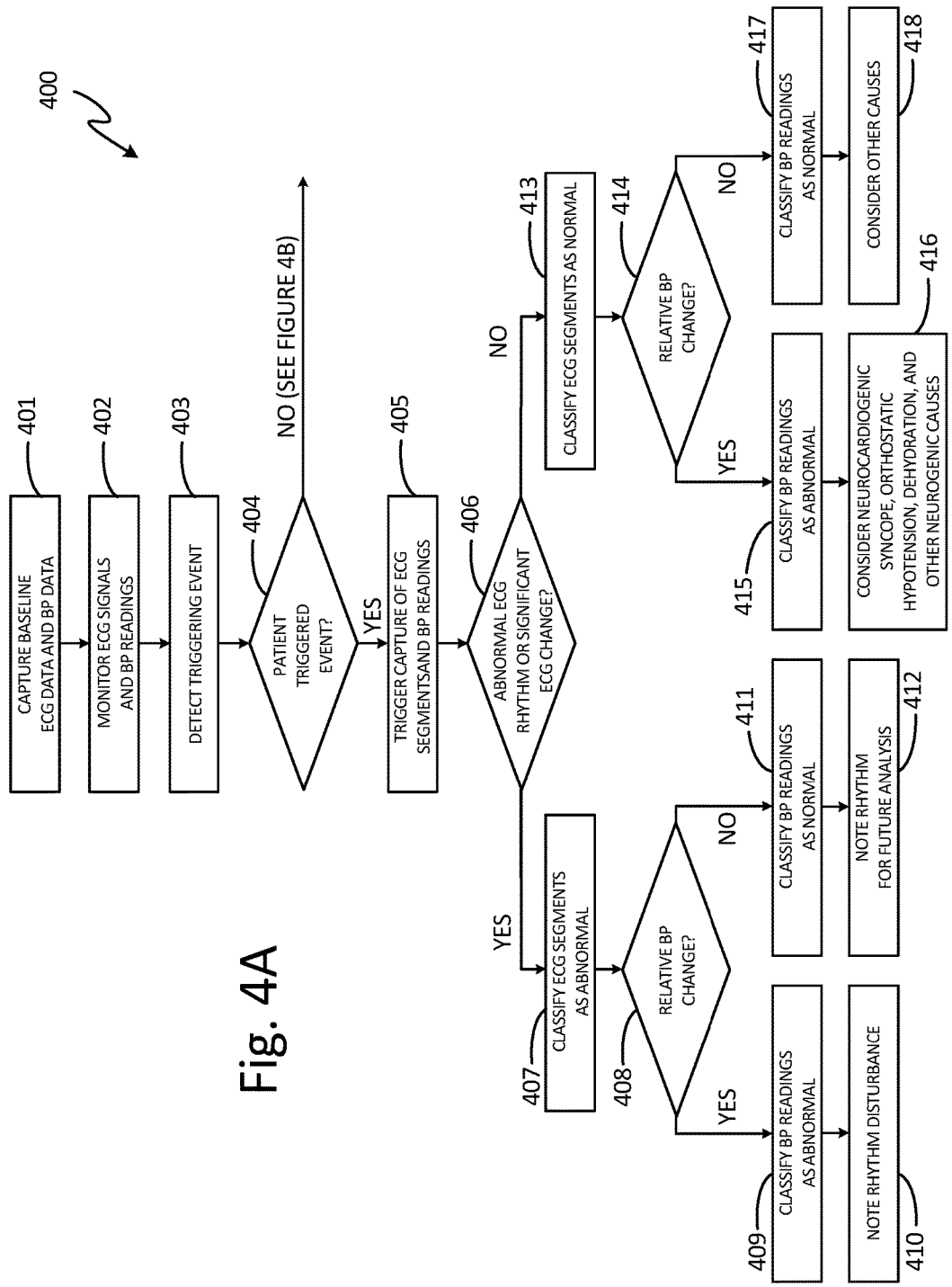
FIGS. 4A and 4B are flowcharts illustrating methods of classifying ECG signals and BP readings as normal or abnormal in response to patient-triggered events and automatically triggered events, respectively, according to one or more embodiments of the present disclosure.
Figure 4B:
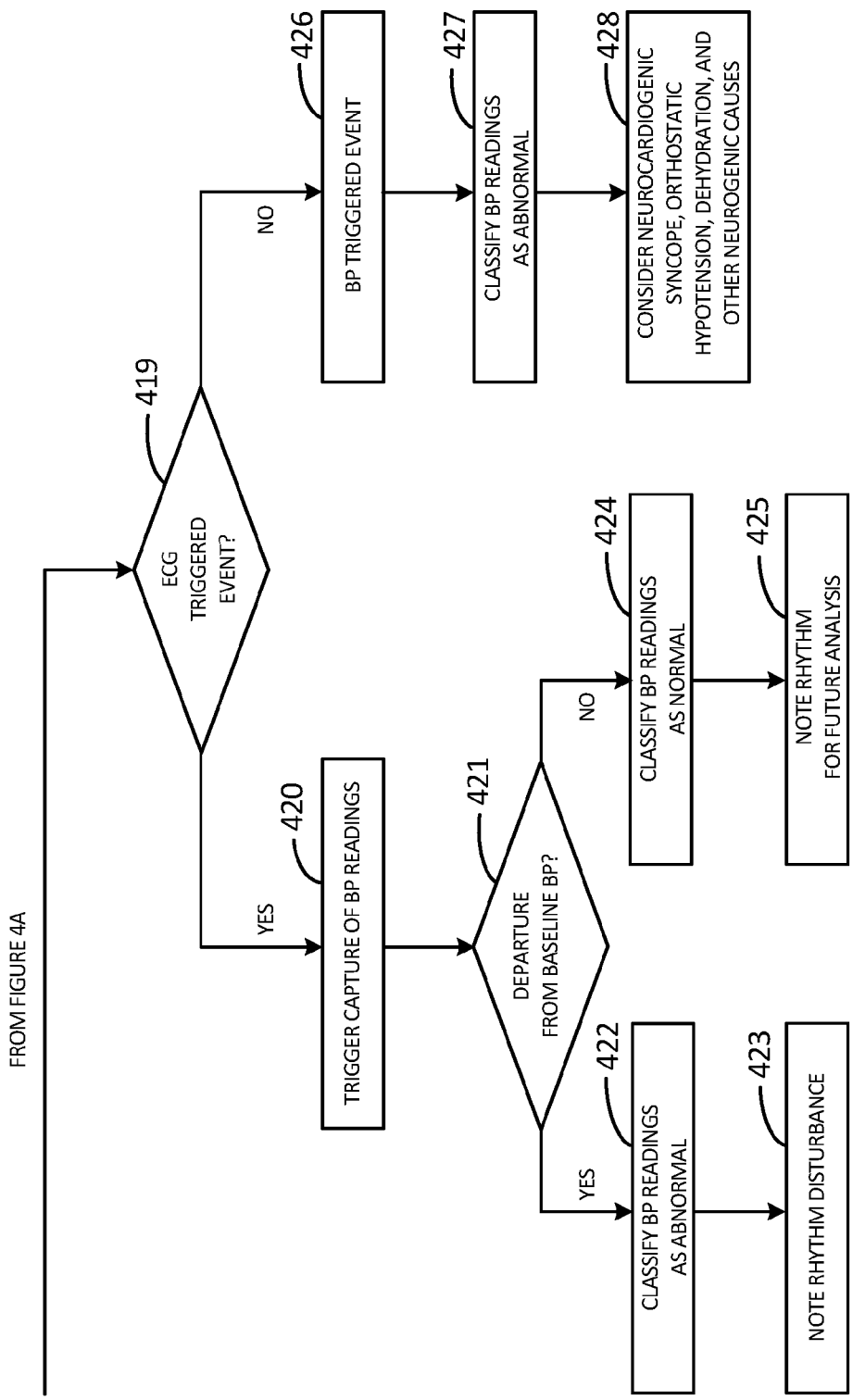

FIGS. 4A and 4B are flowcharts illustrating methods of classifying ECG signals and BP readings as normal or abnormal in response to patient-triggered events and automatically triggered events, respectively, according to one or more embodiments of the present disclosure. Any of the medical devices provided in the present disclosure may be utilized to implement the methods illustrated in FIGS. 4A-4B.

As shown in FIGS. 4A and 4B, at step 401, baseline ECG data and baseline BP data is captured (e.g., collected and stored) from a patient. At step 402, ECG signals and BP are monitored. In some embodiments, monitoring ECG of a patient includes monitoring heart rate. Although step 402 monitors ECG signals and BP of a patient, any of the physiological data provided in the present disclosure may be monitored at this step. At step 403, triggering events are detected. If a triggering event is detected, the method proceeds to step 404. If no triggering event is detected, the method returns to step 402 to monitor ECG signals and BP and continues this loop until a triggering event is detected.

Referring to FIG. 4A, if a patient-triggered event is detected and/or confirmed at step 404, the method 400 proceeds to step 405. At step 405, ECG segments and BP are captured in response to the patient-triggered event.

At step 406, the method determines whether the captured ECG segments are normal or abnormal. In some embodiments, the determination of whether the captured ECG segments are normal or abnormal includes determining whether the captured ECG segment indicates an abnormal ECG rhythm and/or a significant ECG change relative to reference ECG data. In some embodiments, the reference ECG data may include previously captured ECG segments. In other embodiments, the reference data may include any of the baseline data including threshold levels and changes in physiological levels described above with respect to FIGS. 1-3. For example, the reference ECG data may include population-based ECG data.

In embodiments where one or more of an abnormal heart rhythm and significant ECG change is detected at step 406, the method 400 proceeds to step 407 and classifies the captured ECG segment as abnormal. In embodiments where neither an abnormal heart rhythm nor a significant ECG change is detected, the method 400 proceeds to step 413 and classifies the captured ECG segment as normal.

At decision step 408, the method determines whether a relative BP change has occurred. In some embodiments, to determine whether a relative BP change occurred, the captured BP reading is compared to a previously captured BP reading. In one embodiment, the previously captured BP reading is a recently captured BP reading. In other embodiments, the previously captured BP reading is not a recently captured BP reading. In other embodiments, the captured BP reading is compared to one or more of baseline BP data including threshold levels and changes in physiological changes as discussed with respect to FIG. 2. For example, in some embodiments, the captured BP reading is compared to patient-specific baseline blood pressure data.

If a relative change is detected, decision step 408 determines whether the change is sufficient to classify the BP reading as abnormal. In some embodiments, an abnormal BP reading is defined as a sudden increase and/or decrease in blood pressure. In some embodiments, an abnormal BP reading is classified as abnormal if a reduction in systolic BP greater than 20 mmHg from baseline is detected. In another embodiment, an abnormal BP reading is classified as abnormal if a reduction in diastolic BP greater than 10 mmHg from baseline is detected. In other embodiments, any change in BP is sufficient to classify a BP reading as abnormal.

At step 409, if a relative change is detected, the BP reading is classified as abnormal.

At step 410, the captured ECG segments and captured BP readings are both classified as abnormal. In some embodiments, a rhythm disturbance is noted. In some embodiments, the rhythm disturbance is indicative of arrhythmia In other embodiments, the rhythm disturbance is identified as a potential cause of an undiagnosed symptomatic event. In embodiments where syncope is suspected, the rhythm disturbance suggests cardiogenic syncope as a potential cause of the syncopal event. In some embodiments, the classification of both the ECG and BP as abnormal is indicative of a severe health condition requiring immediate medical attention.

If no relative change is detected, decision step 408 proceeds to step 411. At step 411, the captured BP reading is classified as normal.

At step 412, the captured ECG segment is classified as abnormal and the captured BP reading is classified as normal. In some embodiments, heart rhythm is noted for future analysis.

In embodiments where neither an abnormal heart rhythm nor a significant ECG change is detected at step 406, the method 400 proceeds to step 413 and classifies the captured ECG segment as normal.

At decision step 414, the method determines whether a relative BP change has occurred. In some embodiments, to determine whether a relative BP change occurred, the captured BP reading is compared to a previously captured BP reading. In one embodiment, the previously captured BP reading is a recently captured BP reading. In other embodiments, the previously captured BP reading is not a recently captured BP reading. In other embodiments, the captured BP reading is compared to one or more of baseline BP data including threshold levels and changes in physiological changes as discussed with respect to FIG. 2. For example, in some embodiments, the captured BP reading is compared to patient-specific baseline blood pressure data.

If a relative change is detected, decision step 414 determines whether the change is sufficient to classify the BP reading as abnormal. In some embodiments, an abnormal BP reading is defined as a sudden increase and/or decrease in blood pressure. In some embodiments, an abnormal BP reading is classified as abnormal if a reduction in systolic BP greater than 20 mmHg from baseline is detected. In another embodiment, an abnormal BP reading is classified as abnormal if a reduction in diastolic BP greater than 10 mmHg from baseline is detected. In other embodiments, any change in BP is sufficient to classify a BP reading as abnormal.

At step 415, if a relative change is detected, the BP reading is classified as abnormal.

At step 416, the captured ECG segments are classified as normal and the captured BP readings are classified as abnormal. In some embodiments, causes such as neurocardiogenic syncope, orthostatic hypotension, dehydration, and other neurogenic causes are considered. In some embodiments, causes such as neurocardiogenic syncope, orthostatic hypotension, dehydration, and other neurogenic are identified as a potential cause of an undiagnosed symptomatic event.

If no relative change is detected, decision step 414 proceeds to step 417. At step 417, the captured BP reading is classified as normal.

At step 418, the captured ECG segment is classified as normal and the captured BP reading is classified as normal. In some embodiments, this information may be used to rule out causes of undiagnosed symptomatic events. In some embodiments, this information indicates other causes should be considered.

Referring to FIG. 4B, if a patient-triggered event is not detected and/or confirmed at step 404, the method 400 proceeds to step 419 with respect to automatically triggered events.

At step 419, the method 400 determines whether the automatically triggered event is an ECG triggered event, as provided above with respect to FIG. 3. If an ECG triggered event is detected and/or confirmed, the method 400 proceeds to step 420 to trigger capture of BP readings. If an ECG triggered event is not detected and/or confirmed, the method proceeds to step 426 to define the automatically triggered event as a BP triggered event.

In some embodiments, an ECG triggered event may be defined as an ECG above or below a threshold level or a significant change in ECG relative to a baseline ECG level. For example, if monitored ECG signals are above a heart rate threshold in a case of tachycardia or below a heart rate threshold in a case of bradycardia, an ECG triggered event is observed. In this instance, the method proceeds to step 420 to trigger capture of BP readings in response to the ECG triggered event. In some embodiments, the detection and/or confirmation of an ECG triggered event is a sufficient indicator of an abnormal ECG. As a result, the ECG triggered event only triggers capture of BP readings because, based on the occurrence of an ECG triggered event, it is presumed that the ECG is abnormal. In other embodiments (not shown), both ECG segments and BP readings are captured in response to an ECG triggered event. This embodiment generally recognizes that criteria for triggering events may differ from the criteria for abnormal physiological data, and may produce different results. For example, an ECG triggered event based on baseline data may be sufficient as a trigger, but an ECG segment captured in response to the triggered event may be classified as normal relative to reference data (e.g., previously captured ECG segments).

At step 420, BP readings are captured in response to the ECG triggered event.

At decision step 421, the method determines whether a departure from the baseline BP has occurred. In some embodiments, to determine whether the captured BP reading is a departure from the baseline BP, the captured BP reading is compared to baseline BP data. In many embodiments, the captured BP reading is compared to patient-specific BP data. In some embodiments, the baseline BP includes blood pressure thresholds, such as an upper blood pressure limit and a lower blood pressure limit. In other embodiments, the baseline BP data may be based on one or more of reference BP data, such as previously captured BP readings, and baseline BP including threshold levels and changes in physiological changes as discussed above with respect to FIG. 2.

If a departure from baseline BP data is detected, decision step 421 determines whether the change is sufficient to classify the BP reading as abnormal. In some embodiments, an abnormal BP reading is defined as a sudden and/or significant increase and/or decrease in blood pressure relative to baseline data. In some embodiments, an abnormal BP reading is classified as abnormal if a reduction in systolic BP greater than 20 mmHg from baseline is detected. In another embodiment, an abnormal BP reading is classified as abnormal if a reduction in diastolic BP greater than 10 mmHg from baseline is detected. In other embodiments, any change in BP is sufficient to classify a BP reading as abnormal.

At step 422, if a departure from baseline BP data is detected, the BP reading is classified as abnormal.

At step 423, the ECG is presumed abnormal and the captured BP readings are classified as abnormal. In some embodiments, a rhythm disturbance is noted. In some embodiments, the rhythm disturbance is indicative of arrhythmia In other embodiments, the rhythm disturbance is identified as a potential cause of an undiagnosed symptomatic event. In embodiments where syncope is suspected, the rhythm disturbance suggests cardiogenic syncope as a potential cause of the syncopal event. In some embodiments, the classification of both the ECG (presumed) and BP as abnormal is indicative of a severe health condition requiring immediate medical attention.

If no relative change is detected, decision step 421 proceeds to step 424. At step 424, the captured BP reading is classified as normal.

At step 425, the ECG is presumed abnormal and the captured BP reading is classified as normal. In some embodiments, heart rhythm is noted for future analysis.

If an ECG triggered event is not detected and/or confirmed, the method proceeds to step 426 to define the automatically triggered event as a BP triggered event. In one embodiment, at step 426, the method has determined that a triggering event occurred at step 403, that no patient-triggered event occurred at step 404, and that the automatically triggered event was not an ECG triggered event. Through this process of elimination, step 426 must be defined as a BP triggered event. In other embodiments, the process of detecting a triggering event and identifying it as a patient-triggered event and/or automatically triggered event (e.g., ECG triggered event and/or BP triggered event) may be performed in any order.

At step 427, the BP reading is presumed abnormal. In many embodiments, in the absence of any symptomatic events giving rise to a patient-triggered event and in the absence of an ECG triggered event, ECG is presumed normal and no ECG segment is captured. In addition, the occurrence of a BP triggered event is presumed to be a sufficiently reliable indicator an abnormal BP and no BP reading is captured. In embodiments involving a BP triggered event, both the ECG and BP may be presumed normal and abnormal, respectively. While no ECG segments and no BP readings are captured in response to a BP triggered event in the above embodiment, in other embodiments, one or more of ECG segments and BP readings may be captured in response to a BP triggered event.

At step 428, the ECG is presumed normal and the BP is presumed abnormal. In some embodiments, causes such as neurocardiogenic syncope, orthostatic hypotension, dehydration, and other neurogenic causes are considered. In some embodiments, causes such as neurocardiogenic syncope, orthostatic hypotension, dehydration, and other neurogenic are identified as a potential cause of an undiagnosed symptomatic event.

At decision step 405, the captured BP reading is analyzed for purposes of classifying the captured BP reading as normal or abnormal. As provided above with respect to FIGS. 2 and 3, captured physiological data is compared to reference physiological data as a basis for classifying the captured data as normal or abnormal. In some embodiments, captured BP readings are analyzed for a departure from previously captured BP readings. For example, captured BP readings may be analyzed to detect a sudden and/or substantial increase and/or decrease in BP relative to previously captured BP readings. While previously captured BP readings are utilized as reference data in the above embodiments, other embodiments may utilize baseline data for this step. If the BP reading is classified as abnormal, method 400 proceeds to step 406. If the BP is classified as normal, method 400 proceeds to step 408.

Figure 5A:
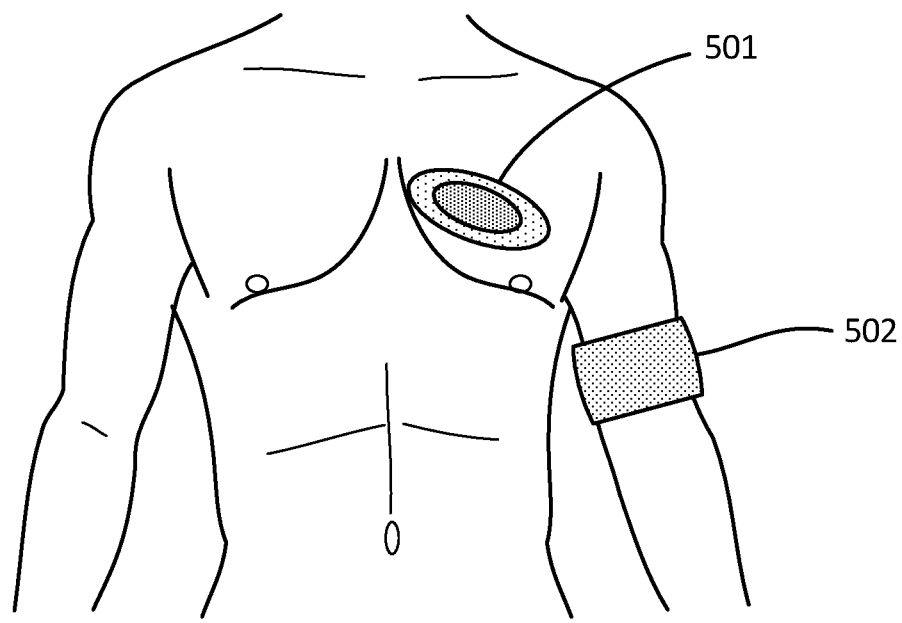
FIGS. 5A and 5B are schematic views of an adherent device with a satellite blood pressure monitor and a satellite blood pressure monitor, respectively, according to one or more embodiments of the present disclosure.
Figure 5B:
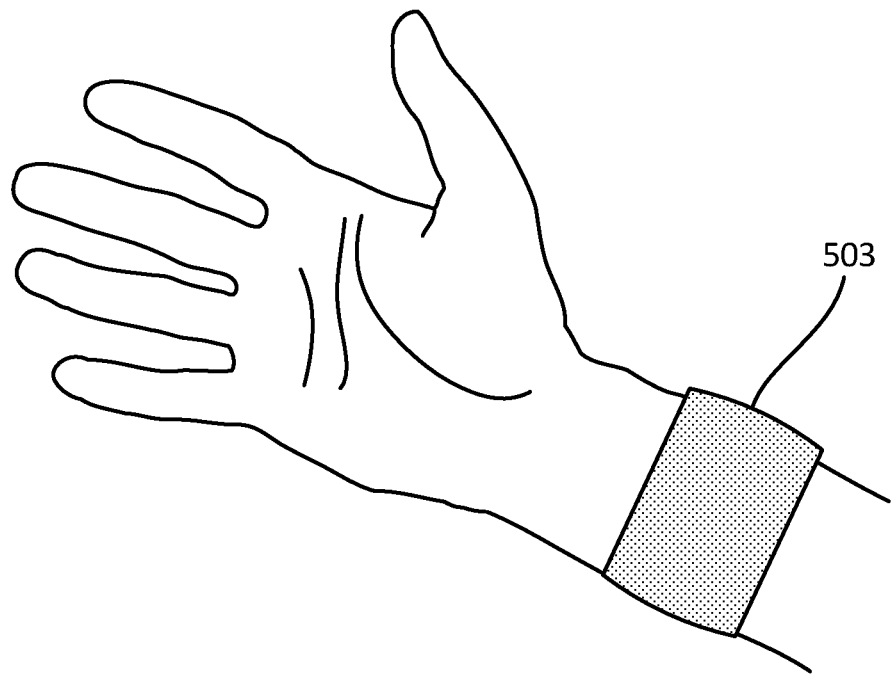

FIGS. 5A-5B is a schematic view of an adherent device a satellite blood pressure monitor, according to one or more embodiments of the present disclosure. As shown in FIG. 5A, an adherent patch 501 is positioned on a thorax of patient P with a satellite blood pressure cuff 502 positioned on an arm of patient P. Another embodiment of a satellite blood pressure cuff is shown in FIG. 5B. In particular, FIG. 5B illustrates a satellite blood pressure cuff 503 worn on a wrist of patient P.

As shown in FIGS. 5A-5B, the blood pressure cuff may monitor and capture BP and the adherent device may monitor and capture ECG (including heart rate). In one embodiment, the monitored and/or captured BP readings are communicated to the adherent device, where the BP readings are combined with the ECG segments. In some embodiments, detecting triggering events is performed locally on the adherent device, but the classification of captured physiological data is performed remotely at a remote monitoring center. In other embodiments, detecting triggering events and/or classifying captured physiological data may be performed locally, remotely, or any combination thereof.

Figure 6:
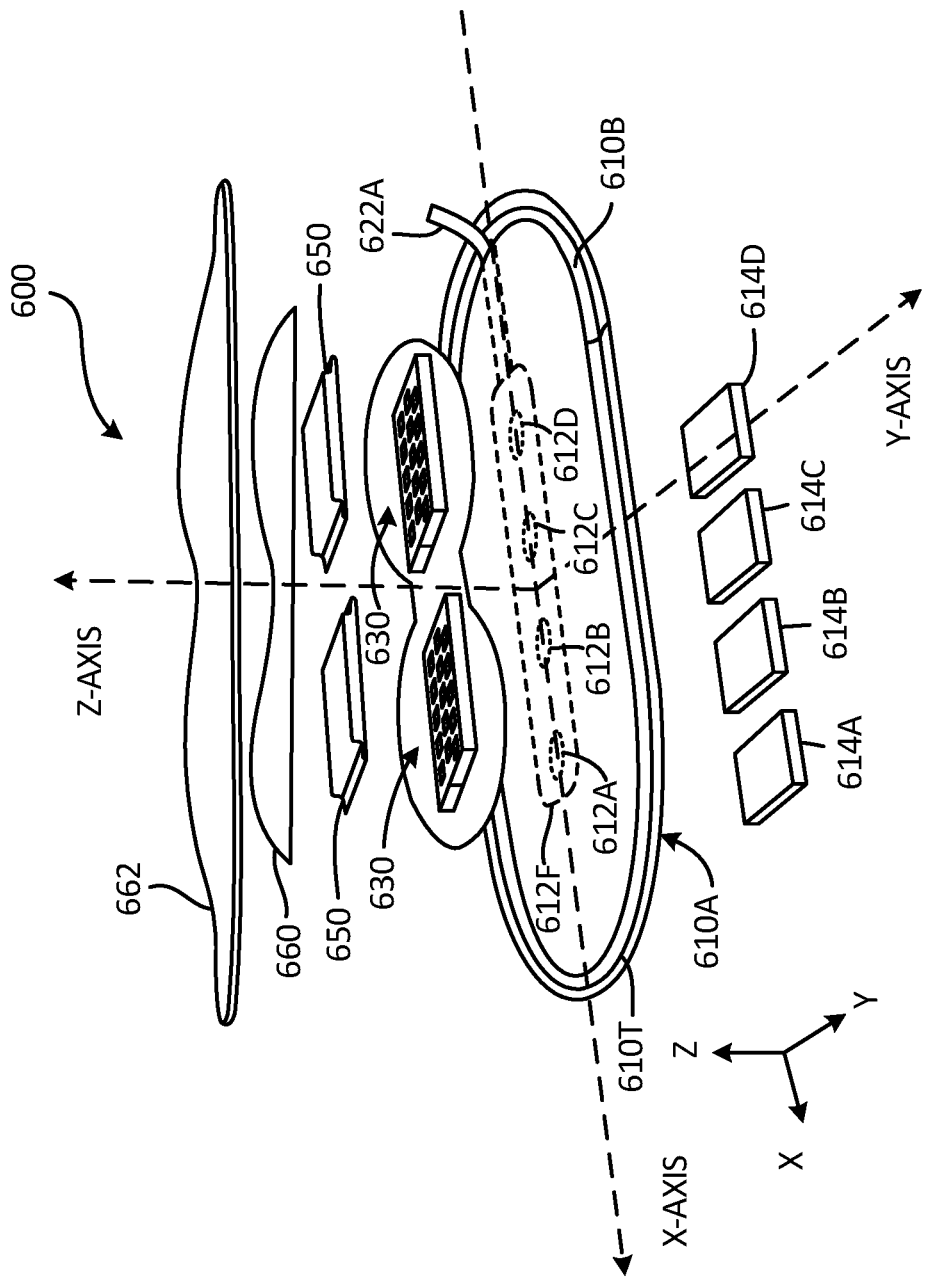
FIG. 6 is a schematic diagram of an adherent device for detecting normal and/or abnormal ECG segments, according to one or more embodiments of the present disclosure.

FIG. 6 is an exploded view of a monitoring device 600, according to an embodiment of the present disclosure. In the embodiment shown in FIG. 6, monitoring device 600 is an adherent device, but, as described above, may also be implemented as an implantable device, an insertable device, an injectable device, or a wearable device. In the embodiment shown in FIG. 6, adherent device 600 includes adherent tape 610T, electrodes 612A, 612B, 612C, 612D with gels 614A, 614B, 614C, 614D, printed circuit board (PCB) 620, flexible connected 622A, electrical components/sensors 630 mounted on PCB 620, batteries 650, electronics housing cover 660, and flexible cover 662.

Adherent device 600 comprises at least two electrodes—although the embodiment shown in FIG. 6 includes electrodes 612A, 612B, 612C and 612D. Adherent device 600 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 600 comprises a first side, or a lower side 610A, that is oriented toward the skin of the patient when placed on the patient. The adherent patch 600 may also comprise a tape 610T which is a material, preferably breathable, with an adhesive (not shown) to adhere to patient P. Electrodes 612A, 612B, 612C and 612D are affixed to adherent patch 600. In many embodiments, at least four electrodes are attached to the patch. Gels 614A, 614B, 614C and 614D can each be positioned over electrodes 612A, 612B, 612C and 612D, respectively, to provide electrical conductivity between the electrodes and the skin of the patient. Adherent patch 600 also comprises a second side, or upper side 610B. In many embodiments, electrodes 612A, 612B, 612C and 612D extend from lower side 610A through adherent patch 100 to upper side 610B. An adhesive can be applied to upper side 610B to adhere structures, for example, a breathable cover, to the patch such that the patch can support the electronics and other structures when the patch is adhered to the patient. In many embodiments, adherent patch 100 may comprise a layer of breathable tape 610T, for example, a tricot-knit polyester fabric, to allow moisture vapor and air to circulate to and from the skin of the patient through the tape. Electrical signals received at electrodes 612A-612D may be communicated to electronic components 630 via flexible connection 622A, which is connected to a PCB (not shown). Cover 660 is positioned over batteries 650 and electronic components 630 to provide protection for both. In addition, flexible cover 662 is positioned to encase the flexible PCB 620, electronics components 630, and/or adherent patch 610 so as to protect at least the electronics components and the PCB In addition, electronic components 630 may include ECG circuitry utilized to generate electrocardiogram signals and data from two or more of electrodes 612A, 612B, 612C and 612D in many ways. In some embodiments, ECG circuitry (not shown) is connected to inner electrodes 612B and 612C, which may comprise sense electrodes of the impedance circuitry. In many embodiments, the ECG circuitry may measure the ECG signal from electrodes 612A and 612D when current is not passed through electrodes 612A and 612D. In addition, electronic components 630 may include bioimpedance circuitry connected to two or more of electrodes 612A, 612B, 612C and 612D to allow electronic components 630 to measure a bioimpedance associated with the patient. In addition, electronic components 630 may include an accelerometer configured to measured motion of the patient.

In addition, electronic circuitry 630 may comprise a processor module. The processor module can be configured to receive physiological parameters from a satellite sensor, such as a blood pressure cuff, and combine the received physiological parameters with physiological parameters monitored and captured by adherent device 600. The processor module can be configured to analyze the physiological parameters according to the methods described herein and also to control the collection and transmission of data received from the electrocardiogram circuitry and circuitry of the satellite sensor. In one embodiment, the processor module is included as part of electronic circuitry 630 and comprises a tangible medium, for example, read only memory (ROM), electrically erasable programmable read only memory (EEPROM) and/or random access memory (RAM). Tangible medium may, for example, store baseline data and/or previously captured data to be utilized in classifying physiological data as normal or abnormal. Processing of monitored physiological parameters such as ECG signals and BP readings may be distributed between the local processor module included as part of electronic circuitry 630 and remote monitoring system 106 (shown in FIG. 1).

In one embodiment, a processor and/or a processing module include electronic circuitry configured to process monitored ECG signals and BP readings of a patient, detect rhythm abnormalities (e.g., bradycardia, tachycardia, etc.) for a plurality of threshold heart rates, capture clinically relevant ECG episode based on the rate-based sensitivity levels associated with each of the plurality of threshold heart rates, adjust the sensitivity of at least one of the sensitivity levels, and reset at least one of the sensitivity levels. The processor and/or processing module may also communicate and/or transmit ECG signals and/or captured ECG segments to a remote monitoring center for review by an analysis.

In many embodiments, electronics components 630 comprise wireless communications circuitry (not shown) to communicate with remote center 106. The PCB (not shown) may comprise an antenna to facilitate wireless communication. The antenna may be integral with the PCB or may be separately coupled thereto. The wireless communication circuitry can be coupled to the electrocardiogram circuitry to transmit to a remote center with a communication protocol at least one of the electrocardiogram signal or other features collected by the adherent device 600. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two-way protocol such that the remote center is capable of issuing commands to control data collection. For example, in one embodiment a physician/technician may push updated heart-rate thresholds and/or rate-based sensitivity levels to adherent device 600. For example, a physician may increase the rate-based sensitivity levels associated with one or more heart-rate thresholds in response to few ECG segments being captured. Conversely, in response to a high number of ECG segments being captured, a physician/expert may decrease the rate-based sensitivity levels associated with one or more heart-rate thresholds.

Discussion of Possible Embodiments

The following are non-exclusive descriptions of possible embodiments of the present invention.

A method of determining an etiology of undiagnosed events, the method comprising monitoring electrocardiogram (ECG) signals and blood pressure (BP) of a patient via a medical device; capturing one or more of an ECG segment and a BP reading in response to a triggering event; classifying one or more of the ECG segment and BP reading as normal or abnormal; and determining etiology of undiagnosed symptomatic events based on the classification of the ECG segment and/or BP reading.

The method of the preceding paragraph can optionally include, additionally and/or alternatively any, one or more of the following features, configurations and/or additional components.

The method may further include wherein the medical device is non-invasive.

The method may further include wherein the medical device includes an adherent patch and a blood pressure cuff.

The method may further include wherein the ECG segment and/or BP reading captured includes one or more of prospectively captured ECG segments, prospectively captured BP readings, recently captured ECG segments, and recently captured BP readings.

The method may further include wherein the triggering event is one or more of a patient triggered event and an automatically triggered event. The method may further include wherein the automatically triggered event is based on the monitored ECG signal and/or BP deviating from baseline data. The method may further include wherein the baseline data includes one or more of patient-specific BP and/or ECG data and population-based BP and/or ECG data.

The method may further include wherein the ECG segment and/or BP reading is classified as normal or abnormal based on reference data.

The method may further include wherein an ECG segment is classified as normal or abnormal based on a previously captured ECG segment.

The method may further include wherein an ECG segment is classified as abnormal if an abnormal heart rhythm is detected.

The method may further include wherein an ECG segment is classified as abnormal if a significant ECG change is detected.

The method may further include wherein a BP reading is classified as normal or abnormal based on a previously captured BP reading.

The method may further include wherein a BP reading is classified as abnormal if a significant BP change is detected.

In another embodiment, a medical device may include sensors for monitoring ECG signals and BP of a patient; circuitry for capturing one or more of ECG segments and BP readings of a patient in response to a triggering event; and a processor for communicating one of more of captured ECG segments and captured BP readings to remote monitoring center directly or indirectly where the captured ECG segments and captured BP readings are classified as normal or abnormal.

The method of the preceding paragraph can optionally include, additionally and/or alternatively any, one or more of the following features, configurations and/or additional components.

The medical device may further include wherein the triggering event is one or more of a patient triggered event and an automatically triggered event. The medical device may further include wherein the automatically triggered events are based on the monitored ECG signal and/or BP deviating from baseline data. The medical device may further include wherein the baseline data includes one or more of patient-specific ECG and/or BP data and population-based ECG and/or BP data.

The medical device may further include sensors for monitoring one or more of glucose levels, pulse pressure, posture, and epidermal pigment.

The medical device may further include wherein an ECG segment is classified as abnormal if an abnormal heart rhythm and/or significant ECG change is detected.

The medical device may further include wherein a BP reading is classified as abnormal if a significant BP change is detected.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A method of determining etiology of undiagnosed events, the method comprising:

monitoring electrocardiogram (ECG) signals of a patient via an adherent device;

capturing an ECG segment in response to a triggering event, wherein the triggering event includes a patient triggered event and/or an automatically triggered event in which the monitored ECG signal deviates from baseline data;

prompting the patient via the adherent device to wear a satellite blood pressure cuff in response to the triggering event, wherein the satellite blood pressure cuff captures blood pressure (BP) readings and communicates the captured BP readings to the adherent device;

communicating the captured ECG segment and captured BP readings from the adherent device to a remote monitoring center;

classifying, at the remote monitoring center, the ECG segment and BP reading as normal or abnormal; and determining etiology of undiagnosed symptomatic events based on the classification of the ECG segment and/or BP reading.

2. The method of claim 1, wherein the ECG segment and/or BP reading captured includes one or more of prospectively captured ECG segments, prospectively captured BP readings, recently captured ECG segments, and recently captured BP readings.

3. The method of claim 1, wherein the baseline data includes one or more of patient-specific ECG data and population-based ECG data.

4. The method of claim 1, wherein the ECG segment and/or BP reading is classified as normal or abnormal based on reference data.

5. The method of claim 1, wherein an ECG segment is classified as normal or abnormal based on a previously captured ECG segment.

6. The method of claim 1, wherein an ECG segment is classified as abnormal if an abnormal heart rhythm is detected.

7. The method of claim 1, wherein an ECG segment is classified as abnormal if a significant ECG change is detected.

8. The method of claim 1, wherein a BP reading is classified as normal or abnormal based on a previously captured BP reading.

9. The method of claim 1, wherein a BP reading is classified as abnormal if a significant BP change is detected.

10. A medical system, the medical system comprising:

an adherent device configured to be adhered to a patient, the adherent device having one or more sensors for monitoring ECG signals of the patient and circuitry for capturing ECG segments in response to a triggering event;

a satellite blood pressure monitor configured to be positioned on the patient's arm for monitoring blood pressure of the patient and capturing BP readings, the satellite blood pressure monitor having communication circuitry for communicating the captured BP readings to the adherent device; and a processor located on the adherent device for communicating one of more of captured ECG segments and captured BP readings to remote monitoring center directly or indirectly where the captured ECG segments and captured BP readings are classified as normal or abnormal;

wherein in response to an automatically triggered ECG event or a patient triggered event, the adherent device prompts the patient to wear the satellite blood pressure monitor to capture BP readings.

11. The medical system of claim 10, wherein the automatically triggered events are based on the monitored ECG signal deviating from baseline data.

12. The medical system of claim 11, wherein the baseline data includes one or more of patient-specific ECG data and population-based ECG data.

13. The medical system of claim 11, wherein the processor on the adherent device compares the monitored ECG signal to the baseline data to identify automatically triggered events.

14. The medical system of claim 10, further comprising sensors for monitoring one or more of glucose levels, pulse pressure, posture, and epidermal pigment.

15. The medical system of claim 10, wherein an ECG segment is classified as abnormal if an abnormal heart rhythm and/or significant ECG change is detected.

16. The medical system of claim 10, wherein a BP reading is classified as abnormal if a significant BP change is detected.

17. The medical system of claim 10, wherein the adherent patch is worn continuously and the satellite blood pressure cuff is worn intermittently.

18. The medical system of claim 10, wherein the remote monitoring center determines an etiology of an syncopal episode based on the classification of the captured ECG segments and captured BP readings as normal or abnormal.

19. The medical system of claim 18, wherein the remote monitoring center a syncopal episode is classified as vasovagal syncope if the captured ECG segment is classified as normal and the captured BP reading is classified as abnormal.

20. The medical system of claim 18, wherein the remote monitoring center a syncopal episode is classified as cardiogenic syncope if the captured ECG segment is classified as abnormal and the captured BP reading is classified as abnormal.

* * * * *